US00PP21655P2

(12) United States Plant Patent
Bernuetz

(10) Patent No.: US PP21,655 P2
(45) Date of Patent: Jan. 18, 2011

(54) ***BRACHYSCOME* PLANT NAMED 'BONBRAHO'**

(50) Latin Name: *Brachyscome multifida*
Varietal Denomination: Bonbraho

(75) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 0 days.

(21) Appl. No.: 12/587,468

(22) Filed: Oct. 7, 2009

(51) Int. Cl.
*A01H 5/00* (2006.01)

(52) U.S. Cl. ..... Plt./411
(58) Field of Classification Search ..... Plt./411
See application file for complete search history.

*Primary Examiner*—Kent L Bell
(74) *Attorney, Agent, or Firm*—C. A. Whealy

(57) ABSTRACT

A new and distinct cultivar of *Brachyscome* plant named 'Bonbraho', characterized by its compact, upright, outwardly spreading and mounding plant habit; freely branching growth habit; uniform and early flowering habit; numerous large inflorescences positioned above the foliage; white-colored ray florets; and good postproduction longevity and garden performance.

1 Drawing Sheet

Botanical designation: *Brachyscome multifida.*
Cultivar denomination: 'Bonbraho'.

BACKGROUND OF THE INVENTION

The present invention relates to a new and distinct cultivar of *Brachyscome* plant, botanically known as *Brachyscome multifida* and hereinafter referred to by the name 'Bonbraho'.

The new *Brachyscome* plant is a product of a controlled breeding program conducted by the Inventor in Yellow Rock, New South Wales, Australia. The objective of the breeding program is to create new mounding *Brachyscome* plants with unique and attractive ray floret color.

The new *Brachyscome* plant originated from a cross-pollination in Yellow Rock, New South Wales, Australia, of a proprietary selection of *Brachyscome multifida* identified as code number 00-95, not patented, as the female, or seed, parent with a proprietary selection of *Brachyscome multifida* identified as code number 00-133, not patented, as the male, or pollen, parent in June, 2004. The new *Brachyscome* plant was discovered and selected by the Inventor as a single flowering plant from within the progeny of the stated cross-pollination in a controlled environment in Yellow Rock, New South Wales, Australia in December, 2004.

Asexual reproduction of the new *Brachyscome* plant by vegetative cuttings in a controlled environment in Yellow Rock, New South Wales, Australia since January, 2005, has shown that the unique features of this new *Brachyscome* plant are stable and reproduced true to type in successive generations.

SUMMARY OF THE INVENTION

Plants of the new *Brachyscome* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Bonbraho'.

These characteristics in combination distinguish 'Bonbraho' as a new and distinct cultivar of *Brachyscome:*

1. Compact, upright, outwardly spreading and mounding plant habit.
2. Freely branching growth habit.
3. Uniform and early flowering habit.
4. Numerous large inflorescences positioned above the foliage.
5. White-colored ray florets.
6. Good postproduction longevity and garden performance.

Plants of the new *Brachyscome* differ from plants of the female parent selection primarily in ray floret color as plants of the female parent selection have light blue-colored ray florets.

Plants of the new *Brachyscome* differ from plants of the male parent selection primarily in inflorescence size as plants of the new *Brachyscome* have larger inflorescences than plants of the male parent selection.

Plants of the new *Brachyscome* can also be compared to plants of the *Brachyscome angustifolia* 'Billabong Mauve Delight', disclosed in U.S. Plant Pat. No. 10,889. In side-by-side comparisons conducted in Yellow Rock, New South Wales, Australia, plants of the new *Brachyscome* differed from plants of 'Billabong Mauve Delight' in the following characteristics:

1. Plants of the new *Brachyscome* were more compact than plants of 'Billabong Mauve Delight'.
2. Plants of the new *Brachyscome* had larger leaves than plants of 'Billabong Mauve Delight'.
3. Leaves of plants of the new *Brachyscome* were deeply pinnatifid whereas leaves of plants of 'Billabong Mauve Delight' were lobed.
4. Plants of the new *Brachyscome* had larger inflorescences with more ray florets per inflorescence than plants of 'Billabong Mauve Delight'.
5. Plants of the new *Brachyscome* and 'Billabong Mauve Delight' differed in ray floret color as plants of 'Billabong Mauve Delight' had violet-colored ray florets.

BRIEF DESCRIPTION OF THE PHOTOGRAPHS

The accompanying colored photographs illustrate the overall appearance of the new *Brachyscome* plant, showing the colors as true as it is reasonably possible to obtain in colored reproductions of this type. Colors in the photographs may differ slightly from the color values cited in the detailed botanical description which accurately describe the colors of the new *Brachyscome* plant.

The photograph at the top of the sheet comprises a side perspective view of a typical flowering plant of 'Bonbraho' grown in a container.

The photograph at the bottom of the sheet is a close-up view of a typical flowering plant of 'Bonbraho'.

DETAILED BOTANICAL DESCRIPTION

The aforementioned photographs and following observations, measurements and values describe plants grown in 15-cm containers in Higashiomi, Shiga, Japan, under commercial practice during the early summer in an outdoor nursery with day temperatures ranging from 10° C. to 25° C. and night temperatures ranging from 6° C. to 15° C. Plants were four months old when the photographs and description were taken. In the following description, color references are made to The Royal Horticultural Society Colour Chart, 2001 Edition, except where general terms of ordinary dictionary significance are used.

Botanical classification: *Brachyscome multifida* 'Bonbraho'.

Parentage:

*Female, or seed, parent.*—Proprietary selection of *Brachyscome multifida* identified as code number 00-95, not patented.

*Male, or pollen, parent.*—Proprietary selection of *Brachyscome multifida* identified as code number 00-133, not patented.

Propagation:

*Type.*—By vegetative cuttings.

*Time to initiate roots, summer.*—About seven days at temperatures of 20° C. to 25° C.

*Time to initiate roots, winter.*—About ten days at temperatures of 15° C. to 20° C.

*Time to produce a rooted young plant, summer.*—About three weeks at temperatures of 20° C. to 25° C.

*Time to produce a rooted young plant, winter.*—About four weeks at temperatures of 15° C. to 20° C.

*Root description.*—Fibrous; white in color.

*Rooting habit.*—Freely branching; moderately dense.

Plant description:

*Plant form and growth habit.*—Compact, upright, outwardly spreading and mounding plant habit; moderately vigorous growth habit; freely branching growth habit with about ten lateral branches per plant; pinching enhances lateral branch development.

*Plant height.*—About 12.7 cm.

*Plant width (spread).*—About 24 cm.

*Lateral branches.*—Length: About 12.9 cm. Diameter: About 1.6 mm Internode length: About 1.3 cm. Strength: Moderately strong. Aspect: Upright to outward. Texture: Smooth, glabrous. Color: Close to 138A.

Foliage description:

*Arrangement.*—Alternate, simple; sessile.

*Length.*—About 3.3 cm.

*Width.*—About 2.5 cm.

*Shape.*—Deeply pinnatifid.

*Apex.*—Acute.

*Base.*—Cuneate.

*Margin.*—Pinnatifid.

*Texture, upper and lower surfaces.*—Smooth, glabrous.

*Venation pattern.*—Pinnate, reticulate.

*Color.*—Developing leaves, upper surface: Close to 144A. Developing leaves, lower surface: Close to 143C. Fully expanded leaves, upper surface: Close to 137A; venation, close to 137A. Fully expanded leaves, lower surface: Close to 137C; venation, close to 137C.

Inflorescence description:

*Appearance and habit.*—Single composite inflorescence form with ray and disc florets arranged acropetally on a capitulum; inflorescences borne above the foliage; uniform and freely flowering habit with about 25 open inflorescences per plant at a time; inflorescences face mostly upright.

*Fragrance.*—None detected.

*Flowering season.*—Plants flower from spring through autumn in Japan; flowering continuous during this period; early flowering habit, plants begin flowering about 35 days after planting.

*Inflorescence longevity.*—Inflorescences last about two to three weeks on the plant; inflorescences persistent.

*Inflorescence bud.*—Height: About 7 mm. Diameter: About 4.4 mm. Shape: Ovoid. Color: Close to 150D.

*Inflorescence size.*—Diameter: About 2.3 cm. Height: About 1 cm. Diameter of disc: About 6.2 mm.

*Ray florets.*—Quantity/arrangement: About 30 to 42 in two or three whorls. Length: About 8.9 mm. Width: About 2.1 mm. Shape: Lanceolate. Apex: Obtuse, praemorse. Base: Obtuse. Margin: Entire. Texture, upper and lower surfaces: Smooth, glabrous. Color: When opening, upper and lower surfaces: Close to 155C. Fully opened, upper and lower surfaces: Close to 155C.

*Disc florets.*—Quantity/arrangement: About 46 massed at center of receptacle. Shape: Tubular, elongated; five-lobed. Apex: Acute. Length: About 4.2 mm. Width: About 1.7 mm. Texture: Smooth, glabrous. Color, immature: Close to 144A. Color, mature: Close to 2A.

*Involucral bracts.*—Quantity/arrangement: About 21; bracts imbricate. Length: About 2.9 mm. Width: About 1.2 mm. Shape: Elliptic to oblong. Apex: Acute. Base: Truncate. Margin: Entire, ciliate. Texture, upper and lower surfaces: Smooth, glabrous. Color, upper and lower surfaces: Close to 143A.

*Peduncles.*—Length: About 4.5 cm. Diameter: About 0.6 mm. Strength: Moderately strong. Texture: Smooth, glabrous. Color: Close to 138A.

*Reproductive organs.*—Androecium: Present on disc florets only. Stamen length: About 1.3 mm. Anther length: Less than 1 mm. Anther shape: Lanceolate. Anther color: Close to 2A. Pollen amount: Moderate. Pollen color: Close to 2A. Gynoecium: Present on ray and disc florets. Pistil length: About 4.5 mm. Stigma shape: Bi-lobed. Stigma color: Close to 2A. Ovary color: Close to 145C. Seeds/fruits: Seed and fruit development has not been observed on plants of the new *Brachyscome.*

Disease/pest resistance: Plants of the new *Brachyscome* have not been observed to be resistant to pathogens and pests common to *Brachyscomes.*

Garden performance: Plants of the new *Brachyscome* have been observed to have good garden performance and tolerate rain, wind and temperatures ranging from about 0° C. to about 40° C.

It is claimed:

1. A new and distinct *Brachyscome* plant named 'Bonbraho' as illustrated and described.

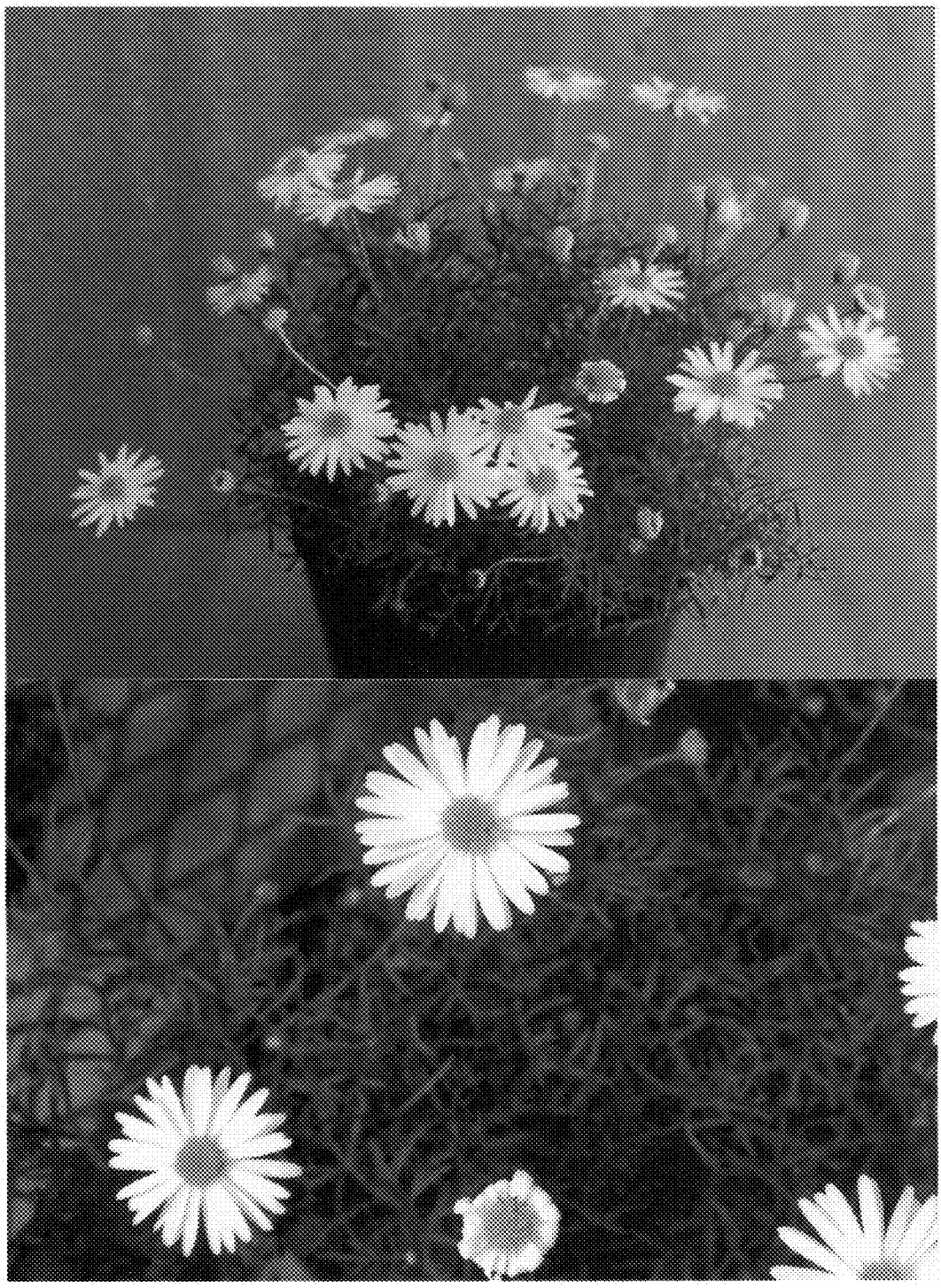

* * * * *